United States Patent [19] [11] 4,182,718
Crutchfield et al. [45] Jan. 8, 1980

[54] 1,3-DIOXOLANE AND 1,3-DIOXANE POLYCARBOXYLATES, AND PRECURSORS THEREOF

[75] Inventors: Marvin M. Crutchfield, St. Louis; Charles J. Upton, Ballwin, both of Mo.

[73] Assignee: Monsanto Company, St. Louis, Mo.

[21] Appl. No.: 844,569

[22] Filed: Oct. 25, 1977

[51] Int. Cl.² .......................................... C07D 319/04
[52] U.S. Cl. .................................. 260/340.7; 252/132; 252/108; 252/175; 260/340.9 R; 560/180; 560/184; 252/535; 252/539; 252/554; 252/558; 252/174.21
[58] Field of Search ...................... 260/340.7, 340.9 R

[56] References Cited

U.S. PATENT DOCUMENTS

| 3,852,306 | 12/1974 | Rapko et al. | 260/340.9 R |
| 3,855,248 | 12/1974 | Lannert et al. | 260/340.9 R |

OTHER PUBLICATIONS

Chem. Abstract 75:99241n.
Chem. Abstract 69:67299x.

*Primary Examiner*—Ethel G. Love
*Attorney, Agent, or Firm*—S. M. Tarter; E. P. Grattan; F. D. Shearin

[57] ABSTRACT

The disclosure relates to:

(a) 1,3-dioxolane and 1,3-dioxane polycarboxylates and their precursors having the general formula:

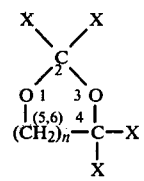

wherein X may be selected from the group consisting of H, $CCl_3$, $CO_2R$, where R is H or lower alkyl, $CO_2M$, where M is alkali metal, preferably Na, $NH_4$ or trialkanolammonium, at least three of the X substituents are other than hydrogen, n is 1 or 2, (b) processes for preparing the compounds and precursors of (a) above by the reaction of a halogenated alcohol with a reactive carbonyl to form a halogenated hemi-ketal or hemi-acetal, followed by the reaction with a base to effect cyclization, (c) detergent compositions comprising additions of carboxylate compounds of (a) to enhance detergency as builders, thresholding agents or the like, and (d) water treating processes comprising contacting water containing hardness ions with amounts of carboxylate compounds of (a) effective to sequester, chelate or bind such ions so as to reduce the water hardness and/or improve operations using the thus treated water.

6 Claims, No Drawings

1,3-DIOXOLANE AND 1,3-DIOXANE POLYCARBOXYLATES, AND PRECURSORS THEREOF

BACKGROUND OF THE INVENTION

The invention relates to salt compounds of 1,3-dioxolane and 1,3-dioxane polycarboxylates, precursors and processes for making such compounds, and detergent compositions and water treating processes utilizing such compounds. The end product compounds are useful as detergent builders, metal chelants, and thresholding agents.

The compounds sequester, complex or otherwise bind metal ions, especially divalent cations such as $Ca^{2+}$ and $Mg^{2+}$ which contribute to water hardness and impede high detergency performance. When incorporated in detergent formulations the compounds improve the cleaning ability of the compositions. The principal uses of the compounds therefore are as detergency builders and/or thresholding agents and as water softeners.

DESCRIPTION OF THE PRIOR ART

In recent years, attention has been directed in the detergent composition field to the development of partial or total replacements for phosphorus-containing detergent builders, such as, sodium tripolyphosphate (STP). As an example, U.S. Pat. No. 3,704,320 issued Nov. 28, 1972 and U.S. patent application Ser. No. 736,962, filed Oct. 29, 1976, now abandoned, each in the name of Kent P. Lannert and assigned to the assignee of this application, describe certain linear ether polycarboxylates having utility as detergent builders.

In addition, the present inventors have jointly investigated certain cyclic polycarboxylates including tetrahydropyran polycarboxylates as described in U.S. patent application Ser. No. 756,947 filed Jan. 5, 1977, now U.S. Pat. No. 4,102,903 and octasodium-1,1,2,2,4,4,5,5-cyclohexane octacarboxylate as described in U.S. patent application Ser. No. 774,171 filed Mar. 3, 1977, now U.S. Pat. No. 4,092,348. The inventors are also aware that the compound:

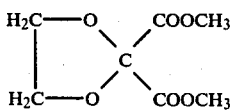

was disclosed in U.S. Pat. No. 3,560,569 and that the compound:

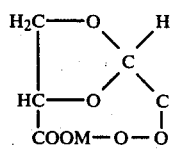

(where M is a divalent metal) has been disclosed in *Journal of the American Chemical Society*, 62, 958 (1940); 63 1447 (1941); and 64, 2435 (1942). Furthermore, U.S. Pat. No. 3,855,248 assigned to the assignee of this application, discloses the compound:

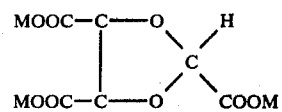

(where M is an alkali metal) useful as a detergent builder.

Also, while processes for basic ketal (acetal) formation have been described in the literature, such processes have not been directed to carboxylate preparations. See Simmons et al J. Am. Chem. Soc. 82, 2288 (1960) and Stedman et al, J. Org. Chem. 33, 1280 (1968).

The present compounds and their method of preparation and properties are readily distinguishable from the above-described compounds and processes.

SUMMARY OF THE INVENTION

The invention relates to:

(a) 1,3-dioxolane and 1,3-dioxane carboxylates and their precursors having the general formula:

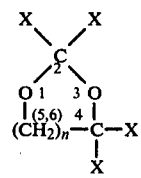

wherein X may be selected from the group consisting of: H, $CO_2R$, where R is H or lower alkyl; $CO_2M$, where M is an alkali metal, $NH_4^+$ or trialkanolammonium; and $CCl_3$, at least three of the X substituents are other than hydrogen, and n is 1 or 2, (b) processes for preparing the compounds of (a) as described herein and generally involving the reaction of a halogenated alcohol with a reactive carbonyl to form a halogenated hemi-ketal or hemi-acetal followed by reaction with a base to effect cyclization, (c) detergent compositions utilizing compounds of (a), and (d) water treatment and/or washing processes utilizing compounds of (a).

The preferred compounds of the invention which are directly useful as detergent builders, water softeners, etc., are the tri- and tetrasodium carboxylates of 1,3-dioxolane and 1,3-dioxane of the formula:

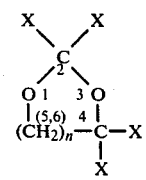

where X is H or COONa and at least three of the X substituents are COONa.

The preparation of the compounds may be generally illustrated by the reactions outlined below:

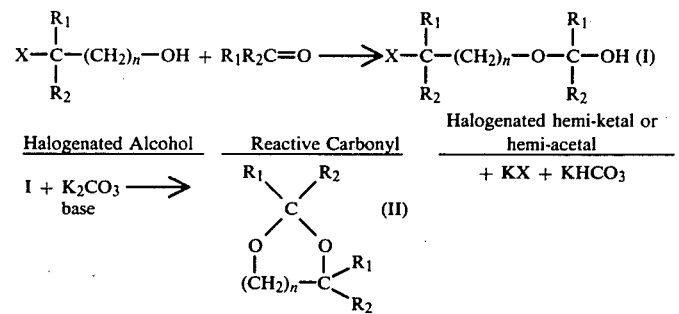

| Halogenated Alcohol | Reactive Carbonyl | Halogenated hemi-ketal or hemi-acetal |

The formula defines dioxolane when n is 1 and the dioxane when n is 2.

In the above reactions X is halogen, i.e., Cl, Br or I, $R_1$ and $R_2$ are H, COOR, where R is lower alkyl, $CCl_3$, etc; n is 1 or 2. When $R_1$ is hydrogen, $R_2$ is other than hydrogen.

DETAILED DESCRIPTION OF THE INVENTION

A. Compounds and Precursor Compounds

The compounds of the invention have molecular structures represented by the formulae:

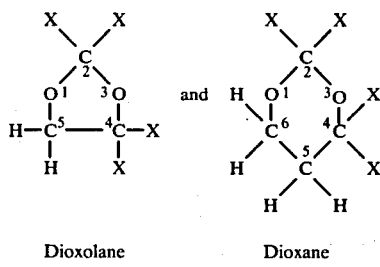

Dioxolane          Dioxane wherein X is H or $CO_2M$, where M is alkali metal, preferably sodium, $NH_4{}^+$ or trialkanolammonium, and at least three of the X substituents are other than H.

The precursor compounds of the invention have the molecular structure represented by the formula:

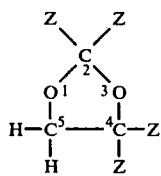

wherein Z is H or COOR and wherein R is lower alkyl, preferably methyl or ethyl or $CCl_3$, at least three of the Z substituents are other than H, and n is 1 or 2.

B. Methods for Synthesizing the Compounds and Precursors

The preparation of the compounds and their precursors is generally set forth above and will be understood more fully by reference to the following detailed examples.

EXAMPLE 1

Preparation of Diethyl 1,3-Dioxolane-2,2-Dicarboxylate

Diethyl ketomalonate 42.0 g (0.24 mol) and 2-chloroethanol 20.5 g (0.24 mol) were added to a 500 ml flask equipped with a stirrer and thermometer and condenser. Reaction to form the hemiketal is mildly exothermic, and the mixture was allowed to stir until the mixture was near room temperature. Hexane (200 ml) was added followed by 33.5 g (0.24 mol) of potassium carbonate. Evolution of $CO_2$ began almost immediately, and continued for approximately 2 hrs. The mixture was allowed to stir overnight at room temperature to insure completion.

The mixture was worked up in the following manner. Water (200 ml) and ether (150 ml) were added. The aqueous and organic phases were separated and the aqueous phase washed with two 100 ml portions ether which were added to the organic phase. The combined organic phase was washed with water, saturated sodium chloride solution and dried over magnesium sulfate. The solution was filtered and concentrated on the rotary evaporator yielding 38.8 g of pale yellow liquid. Distillation in vacuo yielded 30.7 g (52%) of the title compound bp. 92°–94° at 0.2 mm Hg. The structure was confirmed by pmr spectroscopy and GlPC showed the material to be >95% pure.

EXAMPLE 2

Preparation of Disodium 1,3-Dioxolane-2,2-Dicarboxylate

A solution of 11.0 g (0.05 mol) of diethyl 1,3-dioxolane-2,2-dicarboxylate of Example 1 in 50 ml methanol was slowly added to a solution of 8.8 g of 50% aqueous sodium hydroxide (0.11 mol) in 100 ml. methanol. After stirring overnight the mixture was filtered and the salt washed twice with methanol, twice with ether and vacuum dried at 80° yielding 9.9 g (95%) of the title compound as a white solid.

EXAMPLE 3

Preparation of Diethyl 1,3-Dioxane-2,2-Dicarboxylate

The preparation of the title compound follows the general procedure described for the dioxolane analog. Thus 40 g (0.23 mol) diethyl ketomalonate and 35.0 g (0.25 mol) 3-bromo-1-propanol were mixed then reacted with 35 g (0.25 mol) of potassium carbonate and 100 ml benzene solvent. The reaction was somewhat slower than the dioxolane cyclization, thus after 6 hrs., 20 g additional carbonate was added, the temperature raised to 45° and the mixture allowed to stir overnight.

The reaction was worked up as described in Example 1 and after ether removal left 48.9 g of crude product that was distilled in vacuo to give 13.5 g (25%) of the title compound bp 110°-112° at 0.3 mm Hg. The structure was confirmed by pmr, and the sample was >97% pure by GlPC.

EXAMPLE 4

Preparation of Disodium 1,3-Dioxane-2,2-Dicarboxylate

Hydrolysis of 9.0 g (0.039 mol) of diethyl 1,3-dioxane-2,2-dicarboxylate with 6.8 g of 50% aqueous sodium hydroxide as described in Example 2 for the dioxolane analog yielded 8.4 g (0.04 mol) 98% of the title compound as a white free flowing solid.

EXAMPLE 5

Preparation of 1,3-Dioxolane-2,4-Dicarboxylate Esters and Salts (a) Preparation of Methyl-2-Bromo-3-Hydroxypropionate The required haloalcohol precursor was prepared following the general procedure described by Liebman and Fellner, (J. Org. Chem. 27, 438 (1962)). Bromine (0.2 mol) was swept by a nitrogen stream into a stirring solution of methyl acrylate (0.22 mol), silver nitrate (0.2 mol) in water (500 ml) at 0°-2°. The bromine addition was controlled so that the reaction mixture remained only faintly yellow and required 3-5 hrs. When the addition was complete, ether (500 ml) was added and the silver bromide removed by filtration and washed with ether. The filtrate phases were separated and the aqueous phase extracted with four 300 ml portions of ether. The combined ether solution was washed with water, saturated sodium chloride and dried over magnesium sulfate. Concentration on the rotary evaporator left 27 g of a pale yellow liquid shown by pmr and GlPC to be 80-85% of the title compound containing 15-20% methyl 2,3-dibromopropionate. This material was not purified further.

(b) Preparation of Dimethyl 1,3-Dioxolane-2,4-Dicarboxylate

Methyl glyoxylate 11.3 g (0.128 mol) and methyl 2-bromo-3-hydroxypropionate 31 g (0.129 mol) were mixed and the mildly exothermic reaction allowed to cool. The mixture was then treated with hexane (50 ml) and 17.8 g (0.129 mol) potassium carbonate. Evolution of $CO_2$ was sluggish; the mixture was warmed to 45° and allowed to stir overnight. The work-up as described in Example 1 yielded after ether removal, 13.0 g of a light yellow liquid. Distillation in vacuo gave 5.2 g (21%) of the title compound bp 84°-86° at 0.3 mm Hg as a clear colorless liquid. Analysis by GlPC indicated >96% purity, and the pmr spectrum indicated a mixture of trans & cis isomers approximately 70-80% trans.

(c) Preparation of Disodium 1,3-Dioxolane-2,4-Dicarboxylate

To 5.0 g of dimethyl-1,3-dioxolane-2,4-dicarboxylate (Example 5b)) in 100 ml methanol was added a solution of 4.6 g of 50% aqueous sodium hydroxide in 50 ml methanol. After stirring overnight the salt was isolated by filtration and washed with methanol and vacuum dried yielding 2.5 g (42%) of the title compound as a white hygroscopic solid. An additional 1.8 g (30%) could be isolated by addition of ether to the filtrate of the first sample.

(d) Preparation of Methyl-2-Trichloromethyl-1,3-Dioxolane-4-Carboxylate

This compound was prepared as a possible alternate precursor to the title compound of Example 5 (c). Chloral 15.1 g (0.102 mol) and 22 g of methyl 2-bromo-3-hydroxypropionate, as prepared in Example 5(a) were mixed, and after returning to room temperature the mixture was treated with hexane 50 ml and 14.1 g (0.102 mol) potassium carbonate (added in portions over 0.5 hour). After stirring for 6 hours an additional 5 g of potassium carbonate was added and the mixture allowed to stir overnight.

The work-up as described in Example 1 left 23.4 g of crude product after removal of ether. Distillation in vacuo left 17.5 g (69%) of the title compound bp 88°-90° at 0.4 mm Hg. GlPC indicated >99% purity and pmr indicated both trans and cis isomers, 70-75% trans isomer. (Analysis: Calcd for $C_6H_7Cl_3O_4$: %C 28.86, %H 2.80, % Cl 42.68 Found: %C 29.03, %H 2.81, %Cl 42.99).

EXAMPLE 6

(a) Preparation of Methyl Diethyl 1,3-Dioxolane-2,2,4-Tricarboxylate

Diethyl ketomalonate 15 g (0.086 mol) and methyl 2-bromo-3-hydroxy-propionate (Example 5a)) were mixed and after returning to room temperature were treated with hexane (50 ml) and 18.6 g (0.134 mol) potassium carbonate. After 6 hours an additional 5.9 g of carbonate was added and the mixture stirred at 45° overnight.

Work-up as described in Example 1 left 21.0 g of crude product after ether removal. This crude product was combined with that of a 5 g scale run and distilled in vacuo. This yielded 19.7 g (62%) of the title compound, bp 126°-128° at 0.15 mm Hg. The structure was verified by pmr and GlPC indicated the sample to be >97% pure.

(b) Preparation of Trisodium-1,3-Dioxolane-2,2,4-Tricarboxylate

Treatment of 10.0 g (0.036 mol) of methyl diethyl 1,3-dioxolane-2,2,4-tricarboxylate (Example 6a)) with 9.6 g of 50% aqueous sodium hydroxide in 200 ml methanol overnight yielded 11.2 g of product. The pmr, however, indicated the sample to be incompletely hydrolyzed. Complete hydrolysis was effected by dissolving the crude salt in 20 ml $H_2O$ and treating with an additional 1.6 g sodium hydroxide for 0.5 hr. The salt was reprecipitated with methanol (400 ml), filtered, redissolved in water and filtered to remove a trace of insoluble material, precipitated with methanol (400 ml), filtered and vacuum dried. This left 8.2 g (90%) of the title compound as a white powder shown by pmr to be the monohydrate.

(c) Preparation of Diethyl Hydroxymethyl Bromomalonate

This precursor haloalcohol was prepared following the general procedure of Yakubovich and Belyaeva (J. Gen. Chem. USSR 31, 1981 (1961)). A mixture of diethyl bromomalonate 70.0 g (0.29 mol), 37% aqueous formaldehyde, 50 g (0.62 mol) was stirred vigorously and a mixture of pyridine (7 ml) and piperidine (5 ml) added. The mixture was stirred overnight, added to a separatory funnel and the organic layer separated and washed with 10% aqueous sulfuric acid and water. The aqueous phase was washed with two 100 ml portions of ether which was added to the original organic phase and dried over magnesium sulfate. Removal of the solvents under vacuum left 59.1 g (66%) of the title compound, shown by pmr to be 90% pure. This material was used without further purification.

(d) Preparation of Methyl Diethyl 1,3-Dioxolane-2,4,4-Tricarboxylate

The title compound was prepared by reaction of methyl glyoxylate 7.5 g (0.085 mol) and 27 g of diethyl hydroxymethyl bromomalonate (Example 6c)). A small amount (0.3 g) of t-butyl catechol was also added as a polymerization inhibitor. After cooling to room temperature benzene 40 ml and potassium carbonate 11.8 g (0.085 mol) were added. Although $CO_2$ evolution began quickly, the carbonate congealed to a gummy mass. Addition of a second equivalent gave similar results. The solution was decanted, the mass of carbonate washed with three 20 ml portions of benzene. The original solution and washings were then stirred with a third equivalent of carbonate for 60 hrs at 45°. The gummy carbonate residue was also stirred at 25° over 60 hrs., with 20 ml benzene.

The two mixtures were combined and worked up as in Example 1 leaving after solvent removal 29.0 g brown liquid. Distillation in vacuo gave several fractions totalling 7.5 g of 80% pure product, then 7.1 g of 95% pure product bp 125°–127° at 0.3 mm Hg.

(e) Synthesis of Trisodium-1,3-Dioxolane-2,4,4-Tricarboxylate 4.8 g of 50% aqueous sodium hydroxide (0.06 mol) in 50 ml methanol was added to 5.0 g (0.018 mol) of diethyl methyl 1,3-dioxolane-2,4,4-tricarboxylate in 150 ml methanol, and the mixture was stirred overnight. Filtration yielded 4.8 g of product, however, pmr indicated incomplete hydrolysis. The salt was redissolved in 15 ml water, treated with an additional 1.0 g of 50% sodium hydroxide and the solution concentrated at 50° to ca. 7 ml volume. Addition to 300 ml methanol precipitated the salt which was filtered, washed and vacuum dried at 80° and 0.1 mm overnight yielding 4.3 g (80%) of the title compound. The product was shown to be a 1.5 hydrate by pmr.

EXAMPLE 7

(a) Preparation of Tetraethyl 1,3-Dioxolane-2,2,4,4-Tetracarboxylate

Diethyl ketomalonate 15.0 g (0.086 mol) was allowed to react with 28.3 g of 90% pure diethyl hydroxymethyl bromomalonate (Example 6c)). Then benzene 30 ml and potassium carbonate 11.9 g (0.08 mol) was added. After stirring for 4 hours at 40° and additional 6.0 g carbonate was added and the mixture stirred for 48 hours.

Work-up as described for Example 1 left 37.9 g of yellow viscous liquid. Distillation in vacuo gave 21.9 g (70%) of the title compound bp. 165°–170° at 0.4–0.5 mm Hg.

Analysis: Calcd for $C_{15}H_{22}O_{10}$:%C 49.72, %H 6.08. Found=%C 49.62, %H 6.12.

(b) Preparation of Tetrasodium 1,3-Dioxolane-2,2,4,4-Tetracarboxylate

A solution of 9.0 g (0.025 mol) of tetraethyl 1,3-dioxolane 2,2,4,4-tetracarboxylate in 200 ml methanol was treated with 8.8 g (0.109 mol) of 50% aqueous sodium hydroxide in 50 ml methanol and allowed to stir overnight. The salt was filtered, washed and dried to yield 8.7 g of white solid. However, pmr indicated incomplete hydrolysis. A portion, 5.8 g was then treated with 2.5 g 50% aqueous sodium hydroxide overnight in 15 ml water. The mixture was concentrated to about 7 ml volume and added to 200 ml methanol. The salt was filtered, washed and vacuum dried at 80° and 0.2 mm for 8 hrs., to yield 5.7 g (95%) of final product, which contained both water and methanol of hydration.

By a standard test for measuring the binding (sequestering, complexing or chelating) capacity of detergent builder compounds for divalent metal cations ($Ca^{2+}$ and $Mg^{2+}$) associated with water hardness which detract from high detergency performance, the compounds were found to be more effective than dicarboxylic dioxane or dioxolane although not generally as effective as STP. The most effective compound, the tetracarboxylate, is comparable to STP since the millivolt change (A value) of 60 mv is comparable to a typical value of 62±2 mv for STP. These data are summarized in Table I.

TABLE I

| | | CYCLIC ETHER CARBOXYLATES: FIVE-SIX MEMBERED RINGS-TWO OXYGENS | | | | | | | |
|---|---|---|---|---|---|---|---|---|---|
| | | Sequestration*, Divalent Electrode | | | | | Biodegradation | | |
| Example | Structure X = $CO_2Na$ | A (Δmv) | B (Δmv) | C (ml) | D (ml) | % STP | % DOC** | (Weeks) | % $CO_2$*** |
| 2 | (dioxolane with 2 X) | 7 | 6 | 7.0 | 6.0 | 14 | 0 | (10) | — |
| 4 | (dioxane with 2 X) | 11 | 6 | 8.2 | 7.0 | 15 | 0 | (11) | — |
| 5(c) | (dioxolane with X, H, X) | 14 | 4 | 11.5 | 7.7 | 13 | 70 | (7–18) | 57 |
| 6(b) | (dioxolane with X, X, X) | 39 | 9 | 6.7 | 8.0 | 45 | 100 | (3) | 88 |

TABLE I-continued
CYCLIC ETHER CARBOXYLATES: FIVE-SIX MEMBERED RINGS-TWO OXYGENS

| | Structure | Sequestration*, Divalent Electrode | | | | | Biodegradation | | |
|---|---|---|---|---|---|---|---|---|---|
| | | A | B | C | D | | | | |
| Example | X = CO$_2$Na | (Δmv) | (Δmv) | (ml) | (ml) | % STP | % DOC** | (Weeks) | % CO$_2$*** |
| 6(c) | (structure) | 30 | 8 | 7.0 | 8.3 | 34 | 0 | (10) | — |
| 7 | (structure) | 60 | 30 | 7.7 | 9.5 | 71 | 55<br>100 | (0–15)<br>(15–18) | 11 |

*See Matzner et al, Tenside, 10(3), 119–125 (1973) for test details.
**% dissolved organic carbon removal by activated sludge.
***% of theoretical CO$_2$ evolved in CO$_2$ evolution test.

The Divalent Electrode Test Procedure for measuring the binding capacity of detergent builders for divalent cations by an electrode titration method is described by E. A. Matzner et al in an article entitled "Organic Builder Salts as Replacements for Sodium Tripolyphosphate (I)" published in TENSIDE, Vol. 10, 1973, Nos. 3 and 5, pp. 119–125 and 239–245.

In the divalent ion titration A and B are the maximum change in millivolts for Ca$^{2+}$ and Mg$^{2+}$, respectively. C and D are the extrapolated ml of builder solution required to reach the minimum millivolt level.

In biodegradation tests in semi-continuous activated sludge the dicarboxylates are compared with compounds of the present invention. The 24-hour dissolved organic carbon (DOC) removal during the weeks of test, and the CO$_2$ evolution value measured in a 30-day CO$_2$ evolution test are also shown in Table I. A comparison of the data in Table I clearly shows that the tri- and tetracarboxylates of the present invention are better sequestrants, and in many cases far more biodegradable than the dicarboxylate compounds.

C. Compositions Comprising the Compounds of the Invention

In detergency builder applications, the use of the alkali metal salts of the compounds, particularly the sodium salt, is preferred. However, in some formulations (such as liquid formulations where greater builder solubility is required) the use of potassium, ammonium or alkanol ammonium salts may be desirable.

The detergent formulations will contain at least 1% by weight and preferably at least 5% by weight of the salt forms of compounds of this invention. In order to obtain the maximum advantages of the building compositions of this invention, the use of from 5% to 75% of these salts is particularly preferred. The salt compounds of this invention can be the sole detergency builder or these compounds can be utilized in combination with other detergency builders which may constitute from 0 to 95% by weight of the total builders in the formulation. By way of example, builders which can be employed in combination with the novel salt compounds of this invention include water soluble inorganic builder salts such as alkali metal polyphosphates, i.e., the tripolyphosphates and pyrophosphates, alkali metal carbonates, borates, bicarbonates and silicates and water soluble organic builders including amino polycarboxylic acids and salts such as alkali metal nitrilotriacetates, cycloalkane polycarboxylic acids and salts, ether polycarboxylates, alkyl polycarboxylates, epoxy polycarboxylates, tetrahydrofuran polycarboxylates such as 2,3,4,5 or 2,2,5,5-tetrahydrofuran tetracarboxylates, benzene polycarboxylates, oxidized starches, amino(-trimethylene phosphonic acid) and its salts, diphosphonic acids and salts (e.g., methylene diphosphonic acid; 1-hydroxyethylidene diphosphonic acid) and the like.

The detergent formulations will generally contain from 5% to 95% by weight total builder (although greater or lesser quantities may be employed if desired) which, as indicated above, may be solely the builder salt compounds of this invention or mixtures of such compounds with other builders. The total amount of builder employed will be dependent on the intended use of the detergent formulation, other ingredients of the formulation, pH conditions and the like. For example, general laundry powder formulations will usually contain 20% to 60% builder; liquid dishwashing formulations 11% to 12% builder; machine dishwashing formulations 60% to 90% builder. Optimum levels of builder content as well as optimum mixtures of builders of this invention with other builders for various uses can be determined by routine tests in accordance with conventional detergent formulation practice.

The detergent formulations will generally contain a water soluble detergent surfactant although the surfactant ingredient may be omitted from machine dishwashing formulations. Any water soluble anionic, nonionic, zwitterionic or amphoteric surfactant can be employed.

Examples of suitable anionic surfactants include soaps such as the salts of fatty acids containing about 9 to 20 carbon atoms, e.g., salts of fatty acids derived from coconut oil and tallow; alkyl benzene sulfonates—particularly linear alkyl benzene sulfonates in which the alkyl group contains from 10 to 16 carbon atoms; alcohol sulfates; ethoxylated alcohol sulfates; hydroxy alkyl sulfonates; alkenyl and alkyl sulfates and sulfonates; monoglyceride sulfates; acid condensates of fatty acid chlorides with hydroxy alkyl sulfonates and the like.

Examples of suitable nonionic surfactants include alkylene oxide (e.g., ethylene oxide) condensates of mono and polyhydroxy alcohols, alkyl phenols, fatty acid amides, and fatty amines; amine oxides, sugar derivatives such as sucrose monopalmitate; long chain tertiary phosphine oxides; dialkyl sulfoxides; fatty acid amides (e.g., mono or diethanol amides of fatty acids containing 10 to 18 carbon atoms), and the like.

Examples of suitable zwitterionic surfactants include derivatives of aliphatic quaternary ammonium compounds such as 3-(N,N-dimethyl-N-hexadecyl ammonio)propane-1-sulfonate and 3-(N,N-dimethyl-N-hexadecyl ammonio)-2-hydroxy propane-1-sulfonate.

Examples of suitable amphoteric surfactants include betains, sulfobetains and fatty acid imidazole carboxylates and sulfonates.

It will be understood that the above examples of surfactants are by no means comprehensive and that numerous other surfactants are known to those skilled in the art. It will be further understood that the choice and use of surfactants will be in accordance with well understood practices of detergent formulation. For example, anionic surfactants, particularly linear alkyl benzene sulfonate, are preferred for use in general laundry formulations, whereas low foaming nonionic surfactants are preferred for use in machine dishwashing formulations.

The quantity of surfactant employed in the detergent formulations will depend on the surfactant chosen and the end use of the formulation. In general, the formulations will contain from 5% to 50% surfactant by weight, although as much as 95% or more surfactant may be employed if desired. For example, general laundry powder formulations normally contain 5% to 50%, preferably 15% to 25% surfactant; machine dishwashing formulations 0.5% to 5%; liquid dishwashing formulations 20% to 45%. The weight ratio of surfactants to builder will generally be in the range of from 1:12 to 2:1.

In addition to builder and surfactant components, detergent formulations may contain fillers such as sodium sulfate and minor amounts of bleaches, dyes, optical brighteners, soil anti-redeposition agents, perfumes and the like.

In machine dishwashing compositions the surfactant will be a low-foaming anionic or preferably, nonionic surfactant which will constitute 0 to 5% of the formulation.

The term "low-foaming" surfactant connotes a surfactant which, in the foaming test described below, reduces the revolutions of the washer jet-spray arm during the wash and rinse cycles less than 15%, preferably less than 10%.

In the foaming test, 1.5 grams of surfactant is added to a 1969 Kitchen-Aid Home Dishwasher, Model No. KOS-16, manufactured by Hobart Manufacturing Company which is provided with means for counting revolutions of the washer jet-spray arm during wash and rinse cycles. The machine is operated using distilled water feed at a machine entrance temperature of 40° C. The number of revolutions of the jet-spray arm during the wash and rinse cycles is counted. The results are compared with those obtained by operation of the machine using no surfactant change and the percentage decrease in the number of revolutions is determined.

The surfactant should, of course, be compatible with the chlorine containing component hereinafter discussed. Examples of suitable nonionic surfactants include ethoxylated alkyl phenols, ethoxylated alcohols (both mono- and dihydroxy alcohols), polyoxyalkylene glycols, aliphatic polyethers and the like. The widely commercially utilized condensates of polyoxypropylene glycols having molecular weights of from about 1400 to 2200 with ethylene oxide (the ethylene oxide constituting 5 to 35 weight percent of the condensate) are, for example, advantageously used in the machine dishwashing formulations of this invention.

Suitable low-foaming anionic surfactants include alkyl diphenyl ether sulfonates such as sodium dodecyl diphenyl ether disulfonates and alkyl naphthalene sulfonates.

Mixtures of suitable low-foaming surfactants can be utilized if desired.

In addition, machine dishwashing formulations will contain sufficient chlorine providing compound to provide 0.5% to 2% available chlorine. For example, the formulation may contain from 0.5% to 5%, preferably 1% to 3% of a chlorocyanurate or from 10% to 30% chlorinated trisodium phosphate. Suitable chlorocyanurates are sodium and potassium dichlorocyanurates: [(monotrichloro)tetra(monopotassium dichloro)]pentaisocyanate; (monotrichloro) (monopotassium dichloro) diisocyanurate.

Machine dishwashing compositions should additionally contain from 5% to 30% soluble sodium silicate having an $SiO_2$ to $Na_2O$ mole ratio of from 1:1 to 3.2:1, preferably about 2.4:1 to inhibit corrosion of metal parts of dishwashing machines and provide overglaze protection to fine china.

Machine dishwashing compositions will generally contain at least 10%, preferably at least 20% builder, up to a maximum of about 90% builder. The new salt compounds of this invention should constitute at least 5% of the weight of the machine dishwashing formulation.

D. Processes Employing the Compounds of the Invention (a) Washing Processes

The compounds of the present invention are generally employed in washing soiled articles by contacting the article with water in the presence of the compound and preferably also in the presence of one or more detergents. The compound(s) is preferably pre-mixed with the detergent in amounts indicated in the description in "C" above, although it may, of course, be added separately to the wash water.

(b) Water Softening Processes

The softening of water using the compounds of this invention is conducted by contacting the water to be softened with an appropriate amount of the compound to bind the metal ions contributing to the water hardness. The proper amount of compound to soften water from a given source may be determined by using the Divalent Electrode Test Procedure described above.

2. A compound of claim 1 wherein M is sodium.
3. A compound of claim 1 having a molecular structure represented by the formula:
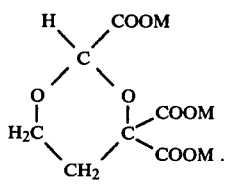
4. A compound of claim 3 wherein M is sodium.
5. The compound of claim 1 having the molecular structure represented by the formula:
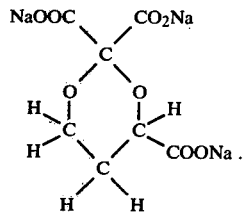
6. The compound of claim 1 having the molecular structure represented by the formula:
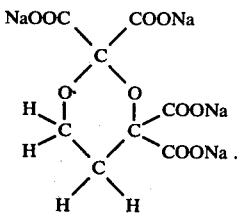

What is claimed is:

1. A compound having a molecular structure represented by the generic formula:

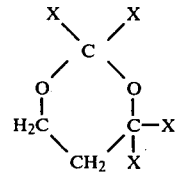

wherein
(a) X is a substituent selected from the group consisting of H and COOM wherein M is selected from the group consisting of alkali metal, $NH_4^+$ and trialkanolammonium; and
(b) at least three of the X substituents in the molecular structure are substituents other than H.